United States Patent [19]

Hoefer

[11] 3,930,880

[45] Jan. 6, 1976

[54] SLAB GEL DIFFUSION DESTAINER

[75] Inventor: Stanton A. Hoefer, San Francisco, Calif.

[73] Assignee: Hoefer Scientific Instruments, San Francisco, Calif.

[22] Filed: Mar. 18, 1974

[21] Appl. No.: 452,076

[52] U.S. Cl.............. 134/111; 134/10; 134/22 R; 134/34; 134/169 R; 134/170; 204/180 G; 204/299
[51] Int. Cl.² ................... B08B 3/10; B08B 11/02
[58] Field of Search............. 134/10, 22 R, 34, 111, 134/147, 154, 166 R, 169 R, 170, 182, 188, 190; 204/180 G, 299

[56] References Cited
UNITED STATES PATENTS

| 3,041,212 | 6/1962 | Booth | 134/111 X |
|---|---|---|---|
| 3,265,078 | 8/1966 | Gordon | 134/166 R |
| 3,500,840 | 3/1970 | Maatz | 134/182 X |
| 3,534,747 | 10/1970 | Hoefer | 134/111 |

Primary Examiner—S. Leon Bashore
Assistant Examiner—Richard V. Fisher
Attorney, Agent, or Firm—Flehr, Hohbach, Test, Albritton & Herbert

[57] ABSTRACT

A destainer for electrophoresis slab gels. The slab gels are placed in flexible mesh, and rolled into cylindrical shapes and inserted into slab holding tubes. The slab holding tubes are placed in the flow path of a washing liquid which flows past the slab gels and then through a return flow path containing a filter for removing stain particles washed away from the slab gels. A magnetic stirring pump draws fluid through the filter forcing it through the slab holding tubes and into the return flow path thereby forming a continuous flow path for destaining slab gels contained entirely within a cylindrical outside container.

10 Claims, 4 Drawing Figures

SLAB GEL DIFFUSION DESTAINER

BACKGROUND OF THE INVENTION

The present invention is directed toward a destainer for slab gels and more specifically toward a destainer which does not disturb the separated protein fractions.

The destaining of acrylimide gels is essential to complete the analysis of proteins which have been separated by electrophoresis. The ionic components of a protein mixture are in an acrylimide gel having a sheet-like configuration. The ionic component separation is not visible to the eye until the gel sheet has been stained and fixed with an appropriate stain. The stain permeates the entire gel rendering it a dense opaque color and the surplus stain, that is all stain which is not held by the ionic bands, must be removed before the bands themselves become visible. Destaining may be implemented electrophoretically by passing direct current through the gel or by diffusion wherein the gel is bathed in a recirculating washing liquid. Electrophoretic destaining runs the risk of imposing band shifts and production of artifacts and requires constant operator attention to the process. Consequently a destaining apparatus and method is needed which does not require constant operator attention and which does not impose band shift within the slab gels.

The diffusion method requires that the stain particles carried away from the gel be absorbed before the liquid is recirculated past the gel to remove remaining stain particles.

OBJECTS AND SUMMARY OF THE INVENTION

In general it is an object of the present invention to provide an improved destainer for electrophoresis slab gels.

It is another object of the present invention to provide for destaining in a relatively short period of time.

It is another object of the present invention to provide a destainer having no component parts extending through the walls of the container wherein the enclosed stirring bar is rotated by a magnetic field applied external to the unit.

It is another object of the present invention to provide a destainer having a closed washing liquid flow path.

It is another object of the present invention to provide a destainer apparatus and method which eliminates band shifts within the slab gels.

It is another object of the present invention to provide a destainer which does not have to be stopped at a precise point in the process.

It is another object of the present invention to provide a destainer which requires a minimum amount of operator time and handling of the slab gels.

The foregoing and other objects of the invention are achieved by a destainer which utilizes a washing liquid which circulates within a liquid container. A flange supported within the container effectively separates the container into first and second compartments. A return flow path extends within the container between the first and second compartments. A filter for removing stain particles is contained within the return flow path. Flexible mesh means for containing gel slabs are provided which may be rolled into cylindrical shapes and placed within slab holding tubes. The slab holding tubes are mounted in openings in the flange so that a pump located in the second container compartment causes washing liquid to flow from the second compartment through the slab holding tubes for removing stain particles from the slab gels. Flow continues through the first compartment to the return path and through the filter which removes stain particles from the washing liquid. The pump draws the filtered liquid from the filter directing it through the second compartment to pass by the slab gels once again in a continuous flow path.

BRIEF DESCRIPTION OF THE PREFERRED EMBODIMENT

Figure 1:
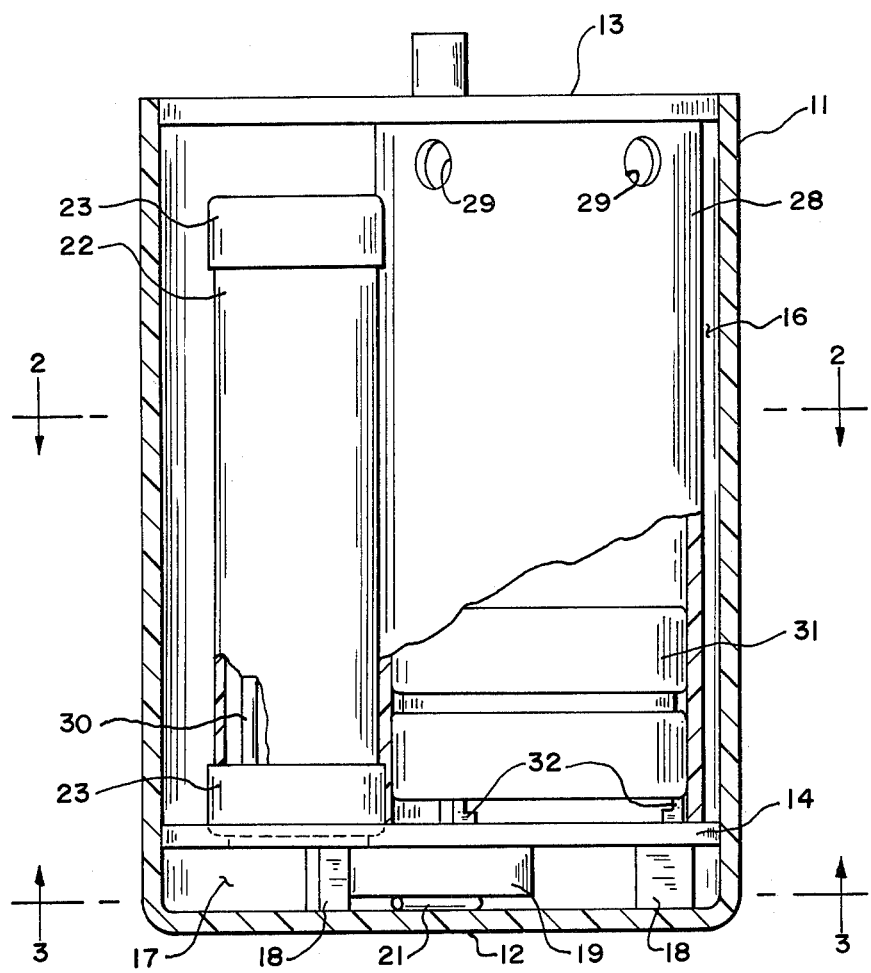
FIG. 1 is a side elevational view partially cutaway of the slab gel diffusion destainer.

Referring to FIG. 1 the slab gel destainer includes a liquid container 11 which is cylindrical in shape having a closed bottom 12 and an open top end. A cover 13 is provided for closing the open top of the container 11. A flange or partition 14 extends across the inside diameter of container 11 effectively dividing the interior of container 11 into a first compartment 16 and a second compartment 17. Partition 14 is supported inside container 11 by feet 18 which rest on the bottom 12. A cylindrical skirt 19 depends from partition 14 but does not extend to the bottom 12. A bar 21 containing magnetic material pivotally rests on the bottom 12 where it is confined within the depending skirt 19.

Figure 3:
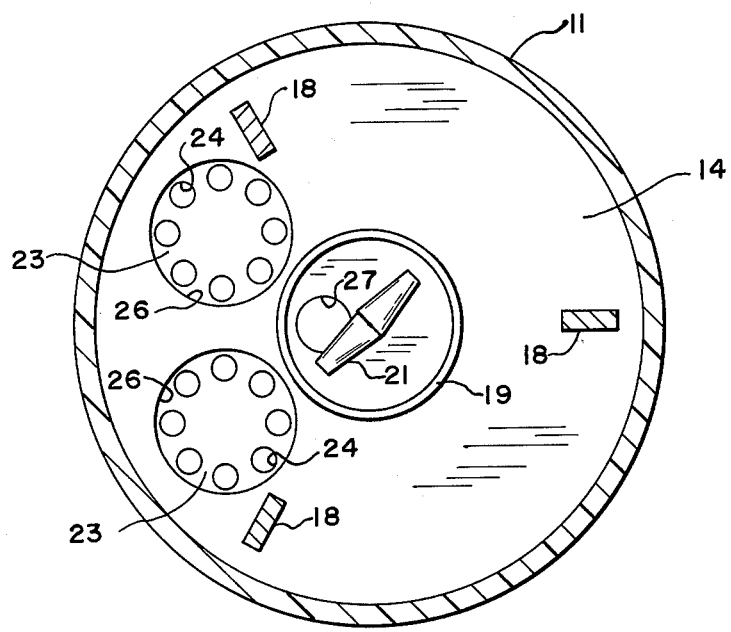
FIG. 3 is a sectional view along the line 3—3 of FIG. 1.

Slab holding tubes 22 are contained within the first compartment and may number one or more. Slab holding tubes 22 are fitted with end caps 23 having perforations 24 therein which may best be seen in FIG. 3. As is also best seen in FIG. 3, partition 14 has openings 26 therethrough which are formed to accept end caps 23. Another opening 27 through partition 14 is located within the area on partition 14 defined by depending skirt 19.

Slab holding tubes 22 are contained within the first compartment and may number one or more. Slab holding tubes 22 are fitted with end caps 23 having perforations 24 therein which may best be seen in FIG. 3. As is also best seen in FIG. 3, partition 14 has openings 26 therethrough which are formed to accept end caps 23. Another opening 27 through partition 14 is located within the area on partition 14 defined by depending skirt 19.

As shown in FIG. 1 cylindrical means 28 is supported on partition 14 having holes 29 communicating first compartment 16 with the interior of cylindrical means 28 which provides a return flow path. A filter 31 substantially fills the inside diameter of cylindrical means 28 supported on blocks 32 at one end thereof.

Figure 2:
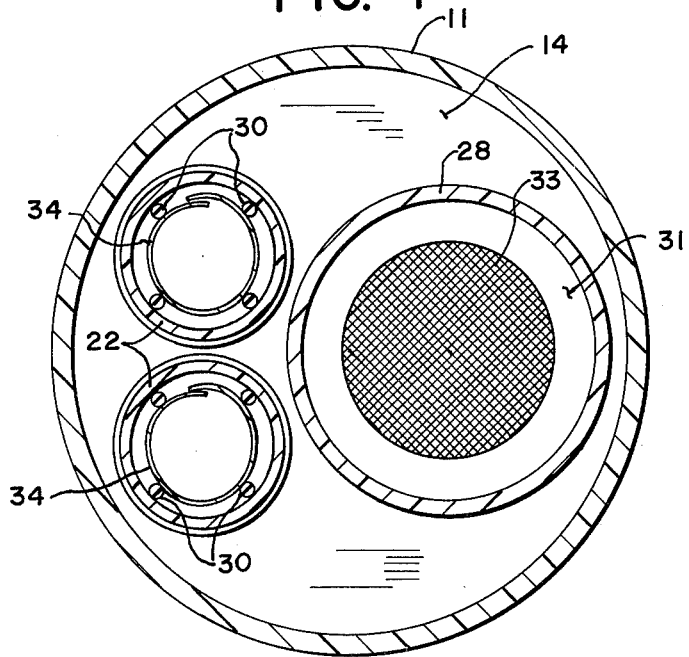
FIG. 2 is a sectional view along the line 2—2 of FIG. 1.

As is best seen in FIG. 2, a number of rods 30 are attached to the inside diameter of slab holding tubes 22 extending along the length of tubes 22. In this embodiment, four rods 30 are spaced at 90° intervals around the inside diameter of tubes 22.

Figure 4:
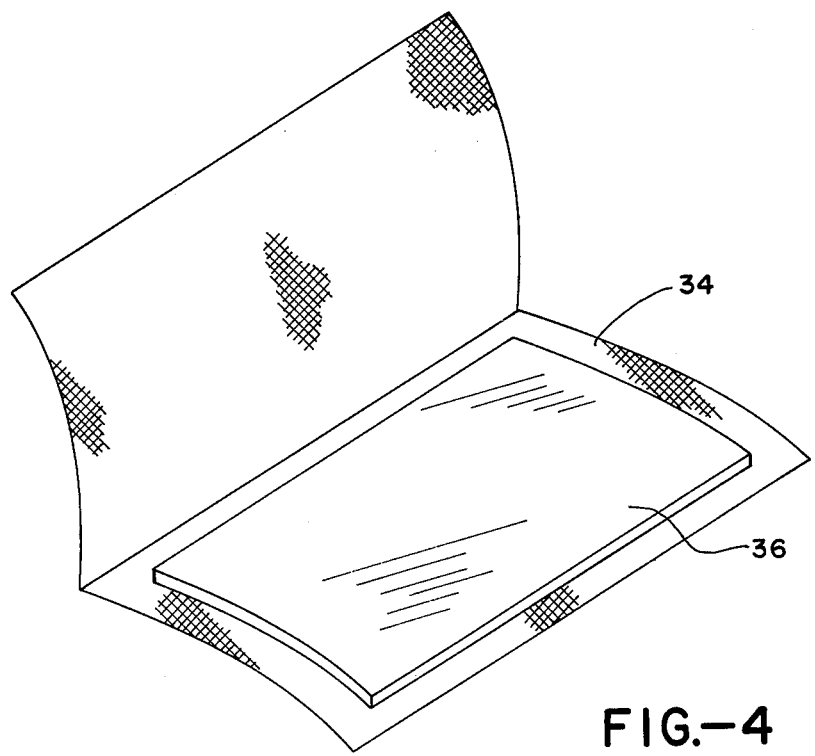
FIG. 4 is an isometric view of a mesh container holding a slab gel.

Referring to FIG. 2 a screen 33 is seen at the inlet end of filter 31 and a similar screen is located at the opposite outlet end. Slab holding tubes 22 contain a folded flexible mesh 34 for containing and supporting the slab gels within the holding tubes 22. FIG. 4 shows a slab gel 36 supported on flexible mesh 34. It may be seen in FIG. 4 that mesh 34 may be folded to contact gel 36 on both sides for supporting and containing gel 36 therein.

Operation of the slab gel diffusion destainer may now be described. Referring to FIG. 4 a slab gel 36 is placed on flexible mesh 34 after electrophoresis for support and containment therein. The mesh 34 is rolled into cylindrical form and inserted in slab holding tube 22 and confined therein by placing end caps 23 on each end. Rods 30 hold the mesh in spaced relation with the inside wall of tubes 22. The slab gel is stained by immersing the slab holding tube 22 in a stain bath whereupon it takes on a dense opaque appearance and is ready for destaining for the purpose of rendering the ionic bands visible. The container 11, cover 13 and all parts included within the confines of the container 11 are of materials which are unaffected by the washing liquid which is circulated through the interior of the destainer. In this embodiment partition 14 may be of polyvinyl chloride and the container 11 is molded TPX (Trademark of International Chemical Industries Ltd. for polymethylpentene). The flexible mesh material is a polypropylene mesh, which in this embodiment may accomodate slabs 36 up to 7 inches wide and 13 inches in length having any desirable thickness. Usual thicknesses range from 0.75mm to 3mm. The slab holding tubes 22 are clear polyvinyl chloride material, and the end caps 23 are polyethylene.

After staining the gel 36 the slab holding tube 22 with end caps 23 attached, is positioned in openings 26 in partition 14. Provision for two such slab holding tubes 22 is shown in this embodiment although any number may be accomodated by appropriate modification of partition 14. Partition 14 supporting gel tubes 22 is placed within container 11 which is filled with an acid destaining solution which functions as the washing liquid. Cover 13 is placed over the open end of container 11 and a rotating magnetic field is applied externally at the bottom 12 of container 11. The bar 21 containing a magnetic material is covered with a material impervious to the washing solution and is rotated by the rotating magnetic field within the confines of depending skirt 19. The rotation of bar 21 pumps the washing liquid centrifugally in second compartment 17 and it passes through openings 26 in partition 14 and perforations 24 in end caps 23 into the interior of slab holding tubes 22. The flow of the washing liquid passes by the inside and outside surfaces of the flexible mesh 34 containing the slab gel 36, as mesh 34 is held away from the inside wall of tube 22 by rods 30. This provides fast uniform flushing and destaining of the slab gel 36. Flow continues through the perforations 24 in the opposite end cap 23 into the first compartment 16. Washing liquid passes through the holes 29 in cylindrical means 28 which provides a return flow path through its interior which contains filter 31. Flow continues through filter 31 and opening 27 in partition 14 to be centrifugally pumped once again by stirring bar 21 into second compartment 17. In this manner a continuous flow path is provided and filtered washing liquid is pumped by all sides of slab gel 36 in slab holding tubes 22 for removing stain particles therefrom.

A slab gel diffusion destainer has been provided which completely destains a 0.75 mm thick gel slab which has been stained with Coomassie Blue in approximately one hour. There is no risk during destining of band shifts or band erasure. Operator handling after loading upon the completion of electrophoresis to the completion of destaining is eliminated. An apparatus is provided containing parts resistant to the washing liquid, as well as a method for destaining slab gels including the steps of supporting a slab gel in a continuous flow path, filtering a destaining liquid in the flow path and pumping the destaining liquid around the flow path.

I claim:

1. A destainer for electrophoresis slab gels utilizing a circulating washing liquid comprising a liquid container having side walls and a bottom wall, a partition supported within said container occupying substantially all of a cross section between the side walls and dividing said container into first and second compartments, said partition having a plurality of openings therethrough, means for defining a return flow path in communication with said first container compartment at one end and with said second container compartment through a first one of said plurality of openings at the other end, filter means mounted in said return flow path and extending across substantially all of a cross section of said return flow path, a plurality of gel slab holders supported by said partition in communication with each of said plurality of openings other than said first one, flexible means permeable to the washing liquid for containing said slab gels, said flexible means being formed for rolling into a cylinder for insertion into said gel slab holders, means for defining a continuous flow path including said means for defining a return flow path and said gel slab holders, and means for circulating the washing liquid through said continuous flow path, whereby substantially all of the washing liquid is circulated past all external surfaces of the slab gels in a filtered condition.

2. A destainer for electrophoresis slab gels utilizing a circulating washing liquid comprising a liquid container having side walls and a bottom wall, a partition supported within said container occupying substantially all of a cross section between the side walls and dividing said container into first and second compartments, said partition having a plurality of openings therethrough including a first opening, means for defining a return flow path in communication with said first container compartment at one end and with said second container compartment through said first opening at the other end, filter means mounted in said return flow path, a plurality of gel slab holding tubes supported by said partition in communication with one each of said plurality of openings other than said first opening, a plurality of perforated caps for covering each end of said holding tubes, said caps being formed to fit within said other openings, flexible means for containing said slab gels for insertion into said gel slab holding tubes, means for defining a continuous flow path including said means for defining a return flow path and said gel slab holders, and means for circulating the washing liquid through said flow path, whereby substantially all of the washing liquid is circulated past the slab gels in a filtered condition, said flexible means for containing the slab gels being rolled into a cylindrical shape prior to insertion into said holding tubes.

3. A destainer for electrophoresis slab gels as in claim 2 wherein said tubes include a plurality of longitudinal members attached to and extending along the inside wall of said holding tubes, whereby said flexible means are held in spaced relation from the inside wall of said holding tubes so that the washing liquid flows past substantially all of the slab gel external surfaces.

4. A destainer for electrophoresis slab gels as in claim 2 wherein said means for circulating the washing liquid comprises a bar containing magnetic material pivoted on said bottom wall of said container and coupled magnetically to an externally applied rotating magnetic field whereby said bar is caused to rotate within said second compartment.

5. A slab gel diffusion destainer utilizing a circulating liquid comprising a liquid container having sidewalls and a bottom wall, means for defining a return flow path within said container, a flange spaced from said bottom wall attached to one end of said means defining said return flow path occupying substantially all of a cross section between said sidewalls and said last named means, said flange having at least first and second openings therethrough, said first opening being in communication with said return flow path, a gel slab holding tube, a flexible mesh for supporting a slab gel on both sides thereof, said flexible mesh being formed to be rolled into a cylinder for insertion into said slab holding tube, perforated caps for covering each end of said holding tube thereby confining said flexible mesh cylinder therein, said holding tube and cap assembly formed to fit in said second flange opening, filter means mounted in said return flow path, and means for circulating the liquid through said first opening, slab gel holding tube, return flow path, and second opening so that when the slab gel is confined in said holding tube and cap assembly and placed in said second flange opening, it is washed until excess stain is removed.

6. A slab gel diffusion destainer as in claim 5 wherein said return path has an axis removed from the axis of said liquid container and the axis of said slab holding tube is parallel to the axis of said return path.

7. A slab gel diffusion destainer as in claim 5 wherein said means for circulating the liquid has a rotating member acting as a centrifugal pump for forcing the liquid away from said filter towards said second flange opening.

8. A slab gel diffusion destainer as in claim 7 wherein said rotating member is pivoted on the bottom wall of said container and is coupled magnetically to an externally applied rotating magnetic field which causes said member to rotate.

9. A slab gel diffusion destainer as in claim 5 wherein the circulating liquid is an acid solution and wherein said liquid container, means for defining a return flow path, flange, slab gel holding tube, flexible mesh, filter means, and means for circulating the liquid are constructed from acid resistant materials.

10. A slab gel diffusion destainer as in claim 5 wherein said gel slab holding tube includes longitudinal members attached to the inside diameter of said holding tube and extending along the length thereof, whereby said flexible mesh is held away from the inside wall of said holding tube so that both sides of the slab gel are washed by the circulating liquid.

* * * * *